(12) United States Patent
Green

(10) Patent No.: US 6,843,980 B2
(45) Date of Patent: *Jan. 18, 2005

(54) METHODS FOR USING ANNEXIN FOR DETECTING CELL DEATH IN VIVO AND TREATING ASSOCIATED CONDITIONS

(75) Inventor: Allan M. Green, Cambridge, MA (US)

(73) Assignee: Theseus Imaging, Corp., Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 10/114,927

(22) Filed: Apr. 3, 2002

(65) Prior Publication Data

US 2002/0192162 A1 Dec. 19, 2002

Related U.S. Application Data

(60) Provisional application No. 60/281,277, filed on Apr. 3, 2001.

(51) Int. Cl.[7] .......................... A61B 10/00; A61B 5/00; A61B 8/00
(52) U.S. Cl. ...................... 424/9.6; 424/1.11; 424/1.65; 424/9.1
(58) Field of Search ............................. 424/1.11, 1.65, 424/9.1, 9.3, 9.4, 9.5, 9.6, 9.7, 9.8; 530/350

(56) References Cited

U.S. PATENT DOCUMENTS

| | | | |
|---|---|---|---|
| 4,671,256 A | 6/1987 | Lemelson .................... | 128/1.1 |
| 5,344,639 A | 9/1994 | Chiu et al. ...................... | 424/9 |
| 5,519,221 A | 5/1996 | Weinberg ............... | 250/363.02 |
| 5,552,525 A | 9/1996 | Dean .......................... | 530/326 |
| 5,627,036 A | 5/1997 | Reutelingsperger ........ | 435/7.21 |
| 5,632,986 A | 5/1997 | Tait et al. .................. | 424/94.64 |
| 5,776,427 A | 7/1998 | Thorpe et al. .............. | 424/1.49 |
| 5,855,866 A | 1/1999 | Thorpe et al. .............. | 424/1.49 |
| 5,863,538 A | 1/1999 | Thorpe et al. ........... | 424/136.1 |
| 5,955,437 A | 9/1999 | Reutelingsperger .......... | 514/21 |
| 5,965,132 A | 10/1999 | Thorpe et al. .............. | 424/149 |
| 5,968,477 A | 10/1999 | Kasina et al. .............. | 424/1.69 |
| 5,976,535 A | 11/1999 | Fritzberg et al. .......... | 424/182.1 |
| 6,004,554 A | 12/1999 | Thorpe et al. ........... | 424/178.1 |
| 6,051,230 A | 4/2000 | Thorpe et al. ........... | 424/178.1 |
| 6,171,577 B1 * | 1/2001 | Kasina et al. .............. | 424/1.69 |
| 6,197,278 B1 | 3/2001 | Blankenberg et al. ..... | 424/1.69 |
| 6,261,535 B1 | 7/2001 | Thorpe et al. .............. | 424/1.49 |
| 6,312,694 B1 | 11/2001 | Thorpe et al. ........... | 424/178.1 |
| 6,323,313 B1 | 11/2001 | Tait et al. ................... | 530/324 |
| 6,406,693 B1 | 6/2002 | Thorpe et al. ........... | 424/130.1 |

FOREIGN PATENT DOCUMENTS

| | | |
|---|---|---|
| WO | WO 92/19279 | 11/1992 |
| WO | WO 94/10149 | 5/1994 |
| WO | WO 95/27903 | 10/1995 |
| WO | WO 95/34315 | 12/1995 |
| WO | WO 96/17618 | 6/1996 |
| WO | WO 98/04294 | 2/1998 |
| WO | WO 00/02587 A1 | 1/2000 |
| WO | WO 00/02584 A2 A3 | 1/2000 |

OTHER PUBLICATIONS

Godar, J. Invest. Dermatology, 1999, vol. 112, pp. 3–12.*
Ohtsuki et al, Eur. J. Nucl. Med., 1999, vol. 26, pp. 1251–1258.*
Blankenberg et al, J. Nucl. Med., Feb. 2001, vol. 42, pp. 309–316.*
Babich, J.W., et al., "Technetium–99m–Labeled Hydrazino Nicotinamide Derivatized Chemotactic Peptide Analogs for Imaging Focal Sites of Bacterial Infection," *The Journal of Nuclear Medicine* 34(11):1964–1974 (1993).
Barrow, S.A., et al., "Localization of Indium–111–Immunoglobulin G, Technetium–99m–Immunoglobulin G and Indium–111–Labeled White Blood Cells at Sites of Acute Bacterial Infection in Rabbits," *The Journal of Nuclear Medicine* 34(11):1975–1979 (1993).
Bennett, M.R., et al., "Binding and Phagocytosis of Apoptotic Vascular Smooth Muscle Cells Is Mediated in Part by Exposure of Phosphatidylserine," *Circ. Res.* 77(6):1136–1142 (1995).
Blankenberg, F.G., et al., "Detection of Apoptotic Cell Death by Proton Nuclear Magnetic Resonance Spectroscopy," *Blood* 87(5):1951–1956 (1996).
Kasina, S., et al., "Preformed Chelate TC–99m Radiolabeling of r–Annexin V for Arterial Thrombus Imaging," *J. of Nuclear Medicine, Proceedings of the 43rd Annual Meeting* 37(5 Supp.):29P Abstract No. 106 (1996).
Koopman, G., et al., "Annexin V for Flow Cytometric Detection of Phosphatidylserine Expression on B Cells Undergoing Apoptosis," *Blood* 84(5):1415–1420 (1994).
Reutelingsperger, C.P.M. et al., "Annexin V, the regulator of phosphatidylserine–catalyzed inflammation and coagulation during apoptosis," *Cell. Mol. Life Sci.* 53:527–532 (1997).
Schwartz, D.A., et al. "Preparation of Hydrazino–Modified Proteins and Their Use for the Synthesis of $^{99m}$Tc–Protein Conjugates," *Bioconjugate Chem.* 2: 333–336 (1991).
Stratton, J.R., et al., "Selective Uptake of Radiolabeled Annexin V on Acute Porcine Left Atrial Thrombi," *Circulation* 92: 3113–3121 (1995).
Tait, J.F., et al., "Site–Specific Mutagenesis of Annexin V: Role of Residues from Arg–200 to Lys–207 in Phospholipid Binding," *Archives of Biochem. and Biophys.* 288(1):141–144 (1991).

(List continued on next page.)

Primary Examiner—Dameron L. Jones
(74) *Attorney, Agent, or Firm*—Lahive & Cockfield, LLP; Maria Laccotripe Zacharakis; Jane E. Remillard, Esq.

(57) ABSTRACT

The present invention provides methods and compositions for imaging cell death in vivo, as well as methods and compositions for tumor radiotherapy.

20 Claims, 2 Drawing Sheets

OTHER PUBLICATIONS

Tait, J.F., et al., "Measurement of membrane phospholipid asymmetry in normal and sickle–cell erthrocytes by means of annexin V binding," *J.Lab. Clin. Med.* 123(5):741–748 (1994).

Tait, J.F., et al., "Phospholipid Binding Properties of Human Placental Anticoagulant Protein–I, a Member of the Lipocortin Family," *The Journal of Biological Chemistry* 264(14):7944–7949 (1989).

Tait, J.F., et al., "Placental Anticoagulant Proteins: Isolation and Comparative Characterization of Four Members of the Lipocortin Family," *Biochemistry* 27:6268–6276 (1988).

Tait, J. F., "Clinical Applications of Annexins," *Annexins: Molecular Structure to Cellular Function,* ed. Barbara A. Seaton, R.G. Landes Co., pp. 213–220 (1996).

van Heerde, W.L., et al., "The Complexity of the Phospholipid Binding Protein Annexin V," *Thrombosis and Haemostasis* 73(2):172–179 (1995).

Wood, B.L., et al., "Increased Erythrocyte Phosphatidylserine Exposure in Sickle Cell Disease: Flow–Cytometric Measurement and Clinical Associations," *Blood* 88(5): 1873–1880 (1996).

Zwaal, R.F.A., et al., "Pathophysiologic Implications of Membrane Phospholipid Asymmetry in Blood Cells," *Blood* 89(4): 1121–1132 (1997).

* cited by examiner

METHODS FOR USING ANNEXIN FOR DETECTING CELL DEATH IN VIVO AND TREATING ASSOCIATED CONDITIONS

RELATED APPLICATIONS

This application claims priority to U.S. Provisional Patent Application Ser. No. 60/281,277 filed Apr. 3, 2001, the entire contents of which are incorporated herein by reference.

BACKGROUND OF THE INVENTION

Apoptosis and Necrosis

Apoptosis refers to "programmed cell death" whereby the cell executes a "cell suicide" program. It is now thought that the apoptosis program is evolutionarily conserved among virtually all multicellular organisms, as well as among all the cells in a particular organism. Further, it is believed that in many cases, apoptosis may be a "default" program that must be actively inhibited in healthy surviving cells.

The decision by a cell to submit to apoptosis may be influenced by a variety of regulatory stimuli and environmental factors (Thompson, 1995). Physiological activators of apoptosis include tumor necrosis factor (TNF), Fas ligand, transforming growth factor β, the neurotransmitters glutamate, dopamine, N-methyl-D-asparate, withdrawal of growth factors, loss of matrix attachment, calcium and glucocorticoids. Damage-related inducers of apoptosis include heat shock, viral infection, bacterial toxins, the oncogenes myc, rel and E1A, tumor suppressor p53, cytolytic T-cells, oxidants, free radicals and nutrient deprivation (antimetabolites). Therapy-associated apoptosis inducers include gamma radiation, UV radiation and a variety of chemotherapeutic drugs, including cisplatin, doxorubicin, bleomycin, cytosine arabinoside, nitrogen mustard, methotrexate and vincristine. Toxin-related inducers or apoptosis include ethanol and d-amyloid peptide.

Apoptosis can have particularly devastating consequences when it occurs pathologically in cells that do not normally regenerate, such as neurons. Because such cells are not replaced when they die, their loss can lead to debilitating and sometimes fatal dysfunction of the affected organ. Such dysfunction is evidenced in a number of neurodegenerative disorders that have been associated with increased apoptosis, including Alzheimer's disease, Parkinson's disease, amyotrophic lateral sclerosis, retinitis pigmentosa and cerebellar degeneration.

The consequences of undesired apoptosis can be similarly devastating in other pathologies as well, including ischemic injury, such as typically occurs in cases of myocardial infarction, reperfusion injury and stroke. In particular, apoptosis is believed to play a central role in very delayed infarction after mild focal ischemia (Du, et al., 1996). Additional diseases associated with increased apoptosis include, but are not limited to, the following: AIDS; myelodysplatic syndromes, such as aplastic anemia; and toxin induced liver disease, including damage due to excessive alcohol consumption.

Necrosis is the localized death of cells or tissue due to causes other than apoptosis (i.e., other than the execution of the cell's intrinsic suicide program). Necrosis can be caused by traumatic injury, bacterial infection, acute hypoxia and the like. There is some overlap between the two types of cell death, in that some stimuli can cause either necrosis or apoptosis or some of both, depending on the severity of the injury.

Asymmetry of Biological Membranes

It is generally believed that biological membranes are asymmetric with respect to specific membrane phospholipids. In particular, the outer leaflet of eukaryotic plasma membranes is formed predominantly with the cholinephospholipids, such as sphingomyelin and phosphatidylcholine (PC), whereas the inner leaflet contains predominantly aminophospholipids, such as phosphatidylserine (PS) and phosphatidylethanolamine (PE). This asymmetry is thought to be maintained by the activity of an adenosine triphosphate (ATP)-dependent aminophospholipid translocase, which selectively transports PS and PE between bilayer leaflets (Seigneuret and Devaux, 1984). Other enzymes thought to be involved in the transport of phospholipids between leaflets include ATP-dependent floppase (Connor, et al., 1992) and lipid scramblase (Zwaal, et al., 1993).

Although asymmetry appears to be the rule for normal cells, the loss of such asymmetry is associated with certain physiological, as well as pathogenic, processes. For example, it has been recognized that membrane asymmetry, detected as appearance of PS on the outer leaflet of the plasma membrane ("PS exposure"), is one of the earliest manifestations of apoptosis, preceding DNA fragmentation, plasma membrane blebbing, and loss of membrane integrity (Martin, et al., 1995; Fadok, et al., 1992).

Similar re-orientation has been observed in sickle cell disease (Lane, et al., 1994)"B-thalassemnia (Borenstain-Ben Yashar, et al., 1993), platelet activation, and in some mutant tumor cell lines with defective PS transport. A gradual appearance of PS on the outer leaflet has also been observed to occur in aging red blood cells (Tait and Gibson, 1994). When the PS exposure on such cells reaches a threshold level, the cells are removed from circulation by macrophages (Pak and Fidler, 1991). All of the above conditions proximately culminate in the death of the affected cells (i.e., cells with significant PS exposure).

It will be appreciated that PS exposure is a component in both apoptosis and necrosis. Its role in the initial stages of apoptosis is summarized above. Once the apoptotic cell has reached the terminal stages of apoptosis (i.e., loss of membrane integrity), it will be appreciated that the PS in both plasma membrane leaflets will be "exposed" to the extracellular milieu. A similar situation exists in cell death by necrosis, where the loss of membrane integrity is either the initiating factor or occurs early in the necrotic cell death process; accordingly, such necrotic cells also have "exposed" PS, since both plasma membrane leaflets are "exposed".

Annexin

Annexin V is normally found in high levels in the cytoplasm of a number of cells including placenta, Lymphocytes, monocytes, biliary and renal (cortical) tubular epithelium. Although the physiological function of annexins has not been fully elucidated, several properties of annexins make them useful as diagnostic and/or therapeutic agents. In particular, it has been discovered that annexins possess a very high affinity for anionic phospholipid surfaces, such as a membrane leaflet having an exposed surface of phosphatidylserine (PS).

SUMMARY OF THE INVENTION

The present invention provides methods and compositions for imaging cell death in vivo, as well as methods and compositions for tumor radiotherapy and phototherapy. The present invention is based, at least in part, on the discovery that the combination of an annexin with a contrast agent allows for the efficient and effective detection of cells undergoing cell death using magnetic reasonance imaging. The present invention is also based, at least in part, on the discovery that the combination of an annexin with an optically active molecule, such as a fluorescent dye, allows for the efficient and effective detection of cells undergoing cell death by optical imaging. Finally, the present invention is based, at least in part, on the discovery that administering a composition comprising an annexin coupled with a therapeutic radioisotope to a tumor bearing subject that has been treated with chemotherapeutic agent, allows for the specific and enhanced delivery of the radiation carried by the annexin-therapeutic radioisotope composition to the tumor site.

Accordingly, the present invention provides a magnetic reasonance imaging composition which includes an annexin, e.g., annexin V, coupled to a contrast agent, such as a paramagnetic agent (e.g., a gadolinium-chelating group complex, such as gadolinium-diethylenetriamine penta-acetic acid, or a lanthanum chelating group complex) or a superparamagnetic agent (e.g., a metal oxide, such as Fe, Co, Ni, Cu, Zn, As, Se, Mo, Tc, Ru, Rh, Pd, Ag, Cd, In, Sn, Re, Os, Ir, Pt, Au, Hg, Tl, Pb, Bi, Po, or At oxide). The metal oxide is preferably coated with a polymer, e.g., dextran or variants thereof. The annexin may be coupled to the contrast agent directly or indirectly.

In another aspect, the present invention provides compositions comprising an annexin, e.g., annexin V, coupled to a contrast agent, such as a polymer coated metal oxide, and a radioisotope, e.g., a diagnostic or therapeutic radioisotope. Such compositions are suitable for both MRI and nuclear medicine imaging. For example, the composition may include annexin V coupled to a contrast agent and a radio-isotope (linked to the annexin via hydrazino nicotinamide (HYNIC)). In one embodiment, the annexin may be coupled to a carrier that is cleared or metabolized by a desirable route. Examples of such carriers include, but are not limited to, dextran particles or colloidal particles or metal oxide particles, such as supelparamagnetic iron oxide particles (which are typically phagocytosed in the liver).

In another aspect, the present invention provides a method for the in vivo imaging of cell death, e.g., cell death caused by apoptosis, in a mammalian subject, for example, in an organ of a mammalian subject or a portion thereof (e.g., brain, heart, liver, lung, pancreas, colon) or a gland of a mammalian subject or a portion thereof (e.g., prostate or mammary gland). The method includes administering to the subject a magnetic reasonance imaging composition comprising annexin coupled to a contrast agent; and obtaining a magnetic reasonance image, wherein said image is a representation of cell death in the mammalian subject. In one embodiment, the magnetic reasonance image is obtained 5, 10, 15, 20, 25, 30, 35, 40, 45, 50, 55, 60, 65, 70, 75, 80, 85, 90, 95, 100, 105, 110, 115, or 120 minutes after the administration of the magnetic reasonance imaging composition to the subject. In another embodiment, the magnetic reasonance image is obtained about 12–30, 15–25, 20–25, or 20–30 hours after the administration of the magnetic reasonance imaging composition to the subject. Ranges intermediate to the above recited values are also intended to be part of this invention. For example, ranges using a combination of any of the above recited values as upper and/or lower limits are intended to be included. In a preferred embodiment, the magnetic reasonance image is obtained at a plurality of time points, thereby monitoring changes in the number of cells undergoing cell death or monitoring changes in the location of cells undergoing cell death.

The magnetic resonance imaging composition may be administered at a concentration of 1–1000 $\mu$g protein/kg, 1–900 $\mu$g protein/kg, 1–800 $\mu$g protein/kg, 1–700 $\mu$g protein/kg, 1–600 $\mu$g protein/kg, 1–500 $\mu$g protein/kg, 1–400 $\mu$g protein/kg, 1–300 $\mu$g protein/kg, 1–200 $\mu$g protein/kg, 1–100 $\mu$g protein/kg, 1–50 $\mu$g protein/kg, or 1–20 $\mu$g protein/kg. In another embodiment, the magnetic reasonance imaging composition is administered intravenously, intraperitoneally, intrathecally, intrapleurally, intralymphatically, or intramuscularly.

In a further aspect, the present invention provides an optical imaging composition which includes an annexin, e.g., annexin V, coupled to a biologically compatible and optically active molecule, such as a fluorescent dye like fluorescein, which can be visualized during optical evaluations such as endoscopy, brochoscopy, peritonoscopy, direct visualization, surgical microscopy and retinoscopy. Moreover, by the appropriate choice of optically active molecule, an annexin-optically active molecule combination may be useful in photodynamic therapy (PDT), a novel approach for the treatment of cancer and other diseases, such as macular degeneration, which may be used as a primary or adjunctive therapeutic modality. In the present invention, PDT works by exposing an annexin molecule linked to a photosensitizing drug to specific wavelengths of light in the presence of oxygen. When this reaction occurs, the normally innocuous photosensitizing molecule becomes cytotoxic via an activated species of oxygen, known as "singlet oxygen." The ability of annexin to localize at sites of tumor cell apoptosis makes this an ideal drug to use in combination with anti-cancer treatment which leads to apoptosis or necrosis of tumor cells. The temporal introduction of the annexin-photosensitizing drug after induction of tumor cell apoptosis or necrosis creates a circumstance for differential localization of the annexin-photosensitizing molecule combination at the tumor site, providing the opportunity for additional tumor cell killing using appropriate light exposure. Typically, laser energy, delivered to the diseased tissue, e.g., cancer site, directly or through a fiberoptic device, chemically activates the drug and creates a toxic form of oxygen which destroys the cancerous cells with minimal damage to healthy cells. Examples of optically active agents which could be used in PDT when linked to annexin include PHOTOFRIN®, Lutrin, ANTRIN®, FOSCAN®, aminolevulinic acid, aluminum (III) phthalocyanine tetrasulfonate, Hypericin, verteporfin, and methylene blue dye. Among the possible targets for PDT are tumors of the brain, head and neck, breast, esophagus, lung, pleural cavity, ovary, abdominal cavity, bladder, prostate, cervix, skin, peritoneal cavity, eye and aerodigestive system.

In yet another aspect, the present invention provides a method for imaging cell death in a mammalian subject in vivo by administering to the subject an optical imaging composition comprising annexin coupled to an optically active molecule; illuminating the subject with a light source; and visually monitoring the presence of the optical imaging composition in the subject, thereby obtaining an image, wherein the image is a representation of cell death in the mammalian subject.

In another aspect, the present invention provides a composition comprising an annexin, e.g., annexin V, coupled with a therapeutic radioisotope, e.g., $^{103}$Pd, $^{186}$Re, $^{188}$Re, $^{90}$Y, $^{153}$Sm, $^{159}$Gd, or $^{166}$Ho. The therapeutic radioisotope and the annexin may be coupled at a ratio of 1:1, 1.1:1, 1.2:1, 1.3:1, 1.4:1, 1.5:1, 1.6:1, 1.7:1, 1.8:1, 1.9:1, or 2:1 (therapeutic radioisotope:annexin). Ranges of values using a combination of any of the above recited values as upper and/or lower limits are intended to be included in the present invention.

In a further aspect, the present invention provides a method of tumor radiotherapy by administering to a mammalian subject having a tumor an effective tumor reducing amount of a composition comprising an annexin coupled with a therapeutic radioisotope. The foregoing method may be used in conjunction with total body irradiation or targeted external irradiation and/or a treatment employing at least one chemotherapeutic agent (e.g., dimethyl busulfan, cyclophosphamide, bischloroethyl nitrosourea, cytosine arabinoside, or 6-thioguanine). In addition, the method may be used in conjunction with biologically active anti-cancer agents and apoptosis inducing agents such as TNF, TRAIL or Fas or with antibodies, small molecules or pharmacophores which bind these receptors and also induce apoptosis.

In another aspect, the present invention features a method of tumor radiotherapy, which includes treating a subject having a tumor with a chemotherapeutic agent and subsequently administering to the subject an effective tumor reducing amount of a composition comprising an annexin coupled with a therapeutic radioisotope.

The timing of the administration of the annexin coupled with a therapeutic agent is critical to the effectiveness of the therapeutic intervention. The modified annexin should be administered at a time which assures its bioavailability at times of apoptosis or necrosis of the target tissue. Diagnostic imaging studies using radiolabeled annexin V indcate that the administration of a therapeutically modified annexin preferably should be within 24 hours of the completion of a course of chemotherapy of lymphoma with multiple anti-metabolite drugs (so-called, CHOP or MOPP therapy) to optimnize the availability of annexin localization in the damaged tumor. Optimal time of administration may be within 72 hours of chemotherapeutic treatment of solid tumors such as breast cancer, lung cancer or sarcoma as shown by imaging studies in patients. Use of a diagnostic imaging agent, such as radiolabeled annexin, to determine the extent of apoptosis may be used to qualify patients for administration of therapeutically modified annexin and to determine the optimal dose of therapeutically modified annexin.

Other features and advantages of the invention will be apparent from the following detailed description, and from the claims.

DETAILED DESCRIPTION OF THE INVENTION

Figure 1:
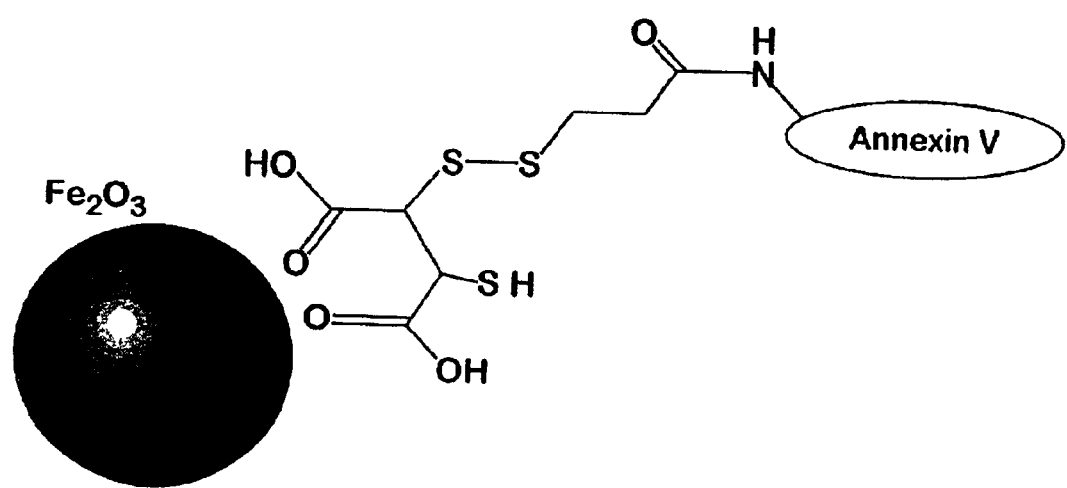
FIG. 1 depicts the attachment of Annexin V to an iron oxide coated with the non-polymer DMSA.
Figure 2:
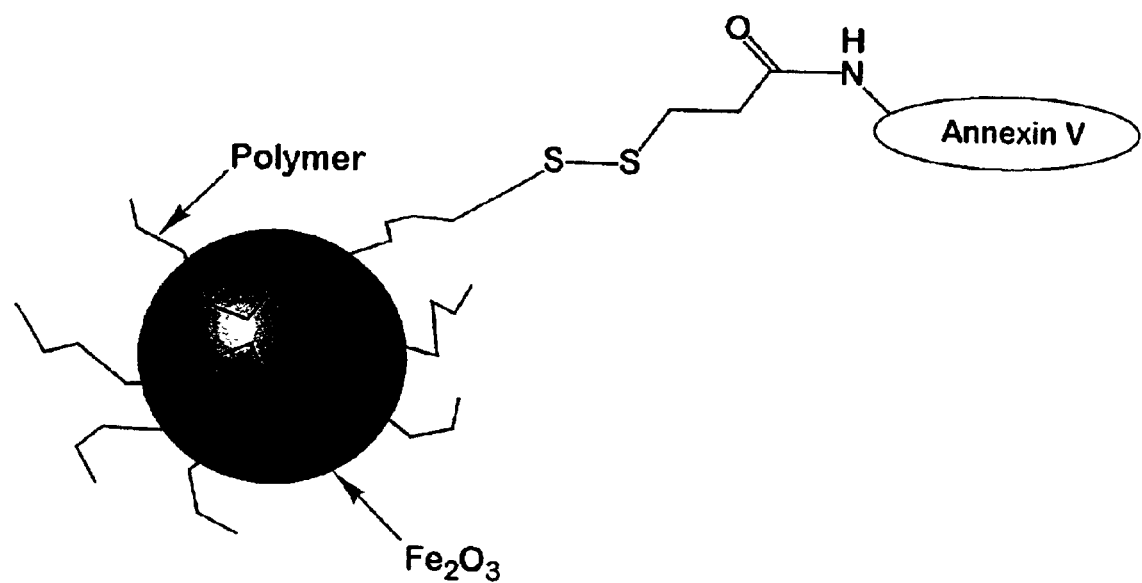
FIG. 2 depicts the attachment of Annexin V to a polymer coated magnetic iron oxide.

The present invention provides methods and compositions for imaging cell death in vivo, as well as methods and compositions for tumor radiotherapy. The present invention is based, at least in part, on the discovery that the combination of an annexin with a contrast agent allows for the efficient and effective detection of cells undergoing cell death using magnetic reasonance imaging. The present invention is also based, at least in part, on the discovery that the combination of an annexin with an optically active molecule, such as a fluorescent dye, allows for the efficient and effective detection of cells undergoing cell death by optical imaging.

Finally, the present invention is based, at least in part, on the discovery that administering a composition comprising an annexin coupled with a therapeutic radioisotope to a tumor bearing subject that has been treated with chemotherapeutic agent, allows for the specific and enhanced delivery of the radiation carried by the annexin-therapeutic radioisotope composition to the tumor site. Without intending to be limited by mechanism, it is believed that the administration of the chemotherapeutic agent will cause apoptosis or necrosis at the site of the tumor, thereby allowing the annexin-therapeutic radioisotope complex to be specifically targeted to the site of the tumor and delivering the radiation, which will kill the cell to which the annexin binds, as well as neighboring cells.

Accordingly, the present invention provides a magnetic reasonance imaging composition which includes an annexin, e.g., annexin V, coupled (either directly or indirectly) to a contrast agent.

As used herein, a "contrast agent" is intended to include any agent that is physiologically tolerable and capable of providing enhanced contrast for magnetic reasonance imaging. Contrast agents typically have the capability of altering the response of a tissue to magnetic fields. Contrast agents include paramagnetic agents, e.g., a gadolinium-chelating group complex, such as gadolinium-diethylenetriamine penta-acetic acid, or a manganese chelating group complex; or biologically compatible superparamagnetic agents such as iron oxide. Contrast agents, such as those described in U.S. Pat. No. 4,687,658; U.S. Pat. No. 5,314,680; and U.S. Pat. No. 4,976,950 are intended to be used in preparing the compositions of the present invention. Contrast agents are commercially available (e.g., the gadolinium chelate Prohance™ is available from Squibb and the gadolinium chelate Dotarem™ is available from Guerbet).

A suitable contrast agent must preferably be biocompatible, e.g., non-toxic, chemically stable, not absorbed by the body or reactive with a tissue, and eliminated from the body within a short time. In one embodiment, the contrast agent may be coupled to a carrier that is cleared or metabolized by a desirable route. Examples of such carriers include, but are not limited to, dextran particles or colloidal particles (which are typically phagocytosed in the liver).

In another aspect, the present invention provides a method for the in vivo imaging of cell death, e.g., cell death caused by apoptosis, in a mammalian subject. The it method includes administering to the subject a magnetic reasonance imaging composition comprising annexin coupled to a contrast agent; and obtaining a magnetic reasonance image, wherein said image is a representation of cell death in the mammalian subject.

As used herein, the term "cell death" includes the processes by which mammalian cells die. Such processes include apoptosis (both reversible and irreversible) and processes thought to involve apoptosis (e.g., cell senescence), as well as necrosis. "Cell death" is used herein to refer to the death or imminent death of nucleated cells (e.g., neurons, myocytes, hepatocytes and the like) as well as to the death or imminent death of a nucleate cells (e.g., red blood cells, platelets, and the like). Cell death is typically manifested by the exposure of PS on the outer leaflet of the plasma membrane.

As used herein, the term "subject" includes warm-blooded animals, preferably mammals, including humans. In a preferred embodiment, the subject is a primate. In an even more preferred embodiment, the subject is a human. Cell death may be imaged or detected in, for example, an organ of a subject or a portion or specimen thereof (e.g., brain, heart, liver lung, pancreas, colon) or a gland of a subject or a portion thereof (e.g., prostate, pituitary or mammary gland). For example, cell death may be imaged or detected using surgical or needle biopsy of a subject after administration of the annexin to the subject; or by the use of a catheter that may detect radiation in a vessel of a subject.

As used herein, the term "administering" to a subject includes dispensing, delivering or applying a composition of the invention to a subject by any suitable route for delivery of the composition to the desired location in the subject, including delivery by either the parenteral or oral route, intramuscular injection, subcutaneous/intradermal injection, intravenous injection, buccal administration, transdermal delivery and administration by the rectal, colonic, vaginal, intranasal or respiratory tract route.

The compositions of the invention may be administered to a subject in an amount effective, at dosages and for periods of time necessary, to achieve the desired result. An effective amount of the compositions of the invention may vary according to factors such as disease state, e.g., the tumor stage, age, and weight of the subject, and the ability of the composition to elicit a desired response in the subject. An effective amount is also one in which any toxic or detrimental effects (e.g., side effects) of the compositions are outweighed by the therapeutically or diagnostically beneficial effects. The compositions of the invention may be administered at a concentration of, for example, 1–1000 μg protein/kg, 1–900 μg protein/kg, 1–800 μg protein/kg, 1–700 μg protein/kg, 1–600 μg protein/kg, 1–500 μg protein/kg, 1–400 μg protein/kg, 1–300 μg protein/kg, 1–200 μg protein/kg, 1–100 μg protein/kg, 10–100 μg protein/kg, 10–80 μg protein/kg, 10–60 μg protein/kg, 10–40 μg protein/kg, or 10–20 μg protein/kg.

The magnetic reasonance image may be obtained using any of the art known techniques, for example, using a Picker Corp. Whole Body Superconducting System operating at 0.3 T using a 30 cm transmitter coil tuned to 0.26 T (10.08 MHz) or other MRI devices with field strengths ranging from 0.05 Tesla to 4.0 Tesla. Typically, the subject is placed in a powerful, highly uniform, static magnetic field. Magnetized protons (hydrogen nuclei) within the subject align like small magnets in this field. Radiofrequency pulses are then utilized to create an oscillating magnetic field perpendicular to the main field, from which the nuclei absorb energy and move out of alignment with the static field, in a state of excitation. As the nuclei return from excitation to the equilibrium state, a signal induced in the receiver coil of the instrument by the nuclear magnetization can then be transformed by a series of algorithms into images. Images based on different tissue characteristics can be obtained by varying the number and sequence of pulsed radiofrequency fields in order to take advantage of magnetic relaxation properties of the tissues.

If it is desired to follow the localization and/or the signal over time, for example, to record the effects of a treatment on the distribution and/or localization of cell death, the imaging can be repeated at selected time intervals to construct a series of images. The intervals can be as short as minutes, or as long as days, weeks, months or years. Images generated by methods of the present invention may be analyzed by a variety of methods. They range from a simple visual examination, mental evaluation and/or printing of a hardcopy, to sophisticated digital image analysis.

The magnetic reasonance image may be obtained 5, 10, 15, 20, 25, 30, 35, 40, 45, 50, 55, 60, 65, 70, 75, 80, 85, 90, 95, 100, 105, 110, 115, or 120 minutes after the administration of the magnetic reasonance imaging composition to the subject. In another embodiment, the magnetic reasonance image is obtained about 10–30, 15–25, 20–25, or 20–30 hours after the administration of the magnetic reasonance imaging composition to the subject. In a preferred embodiment, the magnetic reasonance image is obtained at a plurality of time points, thereby monitoring changes in the number of cells undergoing cell death or monitoring changes in the location of cells undergoing cell death.

The present invention also provides an optical imaging composition which includes an annexin, e.g., annexin V, coupled to an optically active molecule.

As used herein, an "optically active molecule" includes any molecule that has the ability to be optically detected, for example, by the use of medically available visualization devices such as endoscopes, bronchoscopes and minimally invasive surgical devices using optical detection of anatomic structures. Examples of optically detectable molecules include fluorescein and methylene blue. Optically active molecules may also include those agents useful in photodynamic therapy (PDT). PDT works by exposing an annexin molecule linked to a photosensitizing molecule to specific wavelengths of light in the presence of oxygen. When this reaction occurs, the normally innocuous photosensitizing drug becomes cytotoxic via an activated species of oxygen, known as "singlet oxygen." Examples of optically active agents which could be used in PDT when linked to annexin include PHOTOFRIN®, Lutrin, ANTRIN®, FOSCAN®, aminolevulinic acid, aluminum (III) phthalocyanine tetrasulfonate, Hypericin, verteporfin, and methylene blue dye.

In another aspect, the present invention provides a composition comprising an annexin, e.g., annexin V, coupled with a therapeutic radioisotope. As used herein, a "therapeutic radioisotope" is a radioisotope that is recognized as being useful and suitable for injection into a patient for therapeutic applications. A therapeutic radioisotope, as used herein, is preferably an alpha (α) or beta (β) emitting radioisotope. In one embodiment, the therapeutic radioisotope is not a gamma (γ) emitting radioisotope. Examples of therapeutic radioisotopes include $^{103}$Pd, $^{186}$Re, $^{188}$Re, $^{90}$Y, $^{153}$Sm, $^{159}$Gd, or $^{166}$Ho, $^{131}$I, $^{123}$I, $^{126}$I, $^{133}$I, $^{111}$In, and $^{113}$In.

The therapeutic radioisotope and the annexin may be coupled at a ratio of 1:1, 1.1:1, 1.2:1, 1.3:1, 1.4:1, 1.5:1, 1.6:1, 1.7:1, 1.8:1, 1.9:1, or 2:1 (therapeutic radioisotope:annexin). Ranges of values using a combination of any of the above recited values as upper and/or lower limits are intended to be included in the present invention.

In a further aspect, the present invention provides a method of tumor radiotherapy by administering to a mammalian subject having a tumor an effective tumor reducing amount of a composition comprising an annexin coupled with a therapeutic radioisotope. The foregoing method may be used in conjunction with total body irradiation or targeted external irradiation and/or a treatment employing at least one chemotherapeutic agent (e.g., dimethyl busulfan, cyclophosphamide, bischloroethyl nitrosourea, cytosine arabinoside, or 6-thioguanine). The appropriate timing for the administration of the annexin-therapeutic isotope composition may be determined using any of the imaging techniques described herein or the imaging techniques described in U.S. Pat. No. 6,197,278 B1, the contents of which are incorporated herein by reference.

Various aspects of the invention are described in further detail in the following subsections:

Synthesis of Annexin Containing Compounds of the Invention

The invention can be practiced using purified native, recombinant, or synthetically-prepared annexin. Annexin V, for example, may be conveniently purified from human placenta (as described in Funakoshi, et al. (1987) *Biochemistry* 26:5572, the contents of which are incorporated herein by reference). Recombinant annexin offers several advantages, however, including ease of preparation and economic efficiency. A number of different annexins have been cloned from humans and other organisms. Their sequences are available in sequence databases, including GenBank.

The invention is preferably practiced using annexin V, for several reasons. First, annexin V is one of the most abundant annexins, (ii) it is simple to produce from natural or recombinant sources, and (iii) it has a high affinity for phospholipid membranes. Human annexin V has a molecular weight of 36 kd and a high affinity (kd=7 nmol/L) for phosphatidylserine (PS). The sequence of human annexin V can be obtained from GenBank under accession numbers U05760-U05770.

An exemplary expression system suitable for making annexin for use with the present invention employs the pET12a expression vector (Novagen, Madison, Wis.) in *E. coli.* (described in Wood, et al. (1996) *Blood* 88:1873–1880, incorporated herein by reference).

Other bacterial expression vectors may be utilized as well. They include, e.g., the plasmid pGEX (Smith, et al. (1988) *Gene* 67:31) and its derivatives (e.g., the pGEX series from Pharmacia Biotech, Piscataway, N.J.). These vectors express the polypeptide sequences of a cloned insert fused in-frame with glutathione-S-transferees. Recombinant pGEX plasmids can be transformed into appropriate strains of *E. coli* and fusion protein production can be induced by the addition of IPTG (isopropyl-thio galactopyranoside). Solubilized recombinant fusion protein can then be purified from cell lysates of the induced cultures using glutathione agarose affinity chromatography according to standard methods (described in, for example, Ausubel, et al. *Current Protocols in Molecular Biology* (John Wiley and Sons, Inc., Media, Pa.). Other commercially-available expression systems include yeast expression systems, such as the Pichia expression kit from Invitrogen (San Diego, Calif.); baculovirus expression systems (Reilly, et al. in *Baculovirus Expression Vectors: A Laboratory Manual* (1992); Clontech, Palo Alto Calif.); and mammalian cell expression systems (Clontech, Palo Alto Calif.; Gibco-BRL, Gaithersburg Md.).

A number of features can be engineered into the expression vectors, such as leader sequences which promote the secretion of the expressed sequences into culture medium. The recombinantly produced polypeptides are typically isolated from lysed cells or culture media.

Isolated recombinant polypeptides produced as described above may be purified by standard protein purification procedures, including differential precipitation, molecular sieve chromatography, ion exchange chromatography, isoelectric focusing, gel electrophoresis and affinity chromatography. Protein preparations can also be concentrated by, for example, filtration (Amicon, Danvers, Mass.).

Annexin produced as described above may then be coupled to a contrast agent, an optically active molecule, or a therapeutic radioisotope. The particular contrast agent, optically active molecule, or therapeutic radioisotope selected will depend on the particular application the skilled artisan intents to use.

Annexin Radiolabeling

Annexins may be radiolabeled by a variety of methods known in the art (e.g., as described in U.S. Pat. No. 5,985,240; U.S. Pat. No. 4,361,544 and U.S. Pat. No. 4,427,646, the entire contents of each of which are incorporated herein by reference). Annexins may be directly radioiodinated, through electrophilic substitution at reactive aromatic amino acids. Iodination may also be accomplished via pre-labeled reagents, in which the reagent is iodinated and purified, and then linked to the annexin. Iodination may also be achieved through the use of chelates, e.g., DTPA and EDTA chelates, as described in, for example, U.S. Pat. No. 4,986,979; U.S. Pat. No. 4,479,930 and U.S. Pat. No. 4,668,503.

In selecting a suitable therapeutic radioisotope, the skilled artisan will typically consider factors including, but not limited to, (i) minimum of particle emission, (ii) primary photon energy of between about 50 and 500 kEv, (iii) physical half-life greater that the time required to prepare material for administration [Iodine 123 (half-life of ~13.2 hours), Iodine 131 (half-life of ~8 days), Gallium 67 (half-life of ~78 hours), and Indium 111 (half-life of ~2.8 days)], (iv) effective half life longer than the examination time, suitable chemical form and reactivity, low toxicity, and stability or near stability of annexin labeled with that radio-isotope.

Coupling of Annexin to Contrast Agents

Coupling of annexin to contrast agents may be performed using any of the art known techniques, e.g., chemical chelation techniques.

Coupling of annexin to a metal oxide may be performed as described in *Chelating Agents and Metal Chelates*, Dwyer & Mellor, Academic Press (1964), Chapter 7 and U.S. Pat. No. 5,443,816, the contents of each of which are incorporated herein by reference. Ionic forms of the elements iron, cobalt, nickel, copper, zinc, arsenic, selenium, technetium, ruthenium, palladium, silver, cadmium, indium, antimony, rhenium, osmium, iridium, platinum, gold, mercury, thallium, lead, bismuth, polonium and astatine may be used.

For example, annexin may incubated with a first reducing agent, the period of incubation being sufficient to reduce available disulfide bonds to thiolate groups while preventing excessive fragmentation of the annexin; the first reducing agent may then be substantially removed from the thiolate-containing annexin; a source of Sn (II) agent may then be added to the thiolate-containing annexin in a sufficient amount to form Sn (II)-containing and sulfur-containing complexes; and the Sn (II)-containing and sulfur-containing complexes may be labeled by adding the metal oxide, whereby the metal oxide displaces the Sn (II) agent and the metal oxide and thiolate-containing annexin form a complex. The order of the foregoing steps may be altered. For example, it is possible, and in some cases advantageous, to add the Sn (II) to form Sn (II)-containing and sulfur-containing complexes prior to removing excess reducing agent from the thiolate-containing annexin. In this way, oxidation of thiolate groups or reformation of disulfide bonds and other cross-linkages can be minimized.

A compound of the invention may be created by associating annexin with biodegradable superparamagnetic metal oxides such as iron oxide. Annexin associated with superparamagnetic or paramagnetic contrast agents provides the advantage of directing the magnetic resonance contrast agent to those cells which are apoptotic or necrotic. A compound prepared from annexin and biodegradable superparamagnetic iron oxide, for example, binds to hepatocytes which are rendered apoptotic by treatment with fas. A magnetic resonance experiment or imaging procedure carried out after administration to a subject of the compounds of the invention can, thus, provide a method for obtaining an enhanced magnetic resonance image, as well as valuable information regarding the distribution of damaged cells in the organism.

The use of magnetic particles for the attachment of biomolecules has been described by Molday (U.S. Pat. No. 4,452,773, the entire contents of which are incorporated herein by reference). Briefly, a dextran coated magnetic particle is formed and then treated with periodate to produce aldehyde groups. The aldehydes react with amino groups on a biological molecule, to form a Schiff base. The Schiff base may be stabilized by treatment with a reducing agent like sodium borohydride. After treatment with a reducing agent a methylene amino linker connects the biomolecule to the nanoparticle.

Other methods of attaching biomolecules to nanoparticles, which use the reactivity of the aldehyde group, may also be used, including the methods of Rembaum and Owen (see Table I).

The development of amine functionalized crosslinked iron oxide nanoparticle is another method of synthesizing magnetic particle-biomolecule conjugates that may be used to attach annexins to a metal oxide particle. Amino-CLIO is prepared by first synthesizing a dextran coated magnetic nanoparticle, followed by crosslinking the dextran with epichlorohydrin. Amine groups are incorporated by reacting the dextran with ammonia.

Table I (below) summarizes the types of magnetic particles that may be used for the attachement of Annexins, e.g., Annexin V.

efficient targeting to a target cell or organ after injection, they must preferably be in the nanoparticle size range (1–500 nm). Larger particles are rapidly withdrawn from the vascular compartment by the phagocytic cells of the reticuloendothelial system, limiting their ability to react with a limited number of sites on the desired target. Magnetic particles preferably have a narrow size distribution, i.e., cannot have a small percentage of large particles which can occlude capillaries.

(2) Biodegradability. To be useful as a clinical diagnostic tool, magnetic particles must preferably be broken down and excreted or broken down and utilized by the body. Materials like polystyrene, while useful in the synthesis of magnetic particles for cell sorting, cannot be used in parenteral, clinical applications. The most common type of particle used for imaging applications are polymer coated iron oxides, with dextran or modified dextran being most often employed (Anzai (1994) Radiology 192, 709–15; Reimer (1995) Radiology 195, 489; Stark (1988) Radiology 168, 297).

(3) Safety. The magnetic particles must be non-toxic. Typically, the safety factor (the dose used for imaging divided by the dose killing 50% of a group of animals) is greater than 100 and preferably greater than 1000. Toxicity includes not only the generation of reversible or irreversible tissue damage, but also the induction of transient but annoying physiological reactions in selected subjects (such as humans) taking the preparation. These include fever, uticaria, mild pain, vomiting, and the like. To be useful as a clinical diagnostic agent, such as an MR imaging agent, the magnetic particle must preferably produce no discernable physiological response, except for the desired diagnostic information, in individuals taking preparation.

(4) Stability. To be used as a parenteral agent, the particle must preferably maintain its size distribution during a

TABLE I

Magnetic Particles That Can Be Used for the Attachment of Annexins

| Particle Size | Attachment Chem/ Biomolecule Attached | Polymer | Reference |
| --- | --- | --- | --- |
| <100 nm | Periodate/antibody | Dextran | Abts (1989) J. Immunol Methods 125, 19. |
| 10–70 nm/ dextran | Periodate/antibody | Dextran | U.S. Pat. No. 4,452,773 (Molday); Molday, (1982) J. Immunol. Methods 52, 353. |
| 10–200 nm/ albumin | SPDP/antibody | BSA | U.S. Pat. No. 4,795,698 (Owen) |
| 10–50 nm | Periodate/Synaptotagmin 1 | Carboxy Dextran | Zhoe (2001) Nat. Med. 7, 1241. |
| 40 nm | SPDP.Oligonucleotides and Peptides | Crosslinked Dextran | Josephson (1999) Bioconjug. Chem. 10, 186. |
| 10–200 nm | Aldehydes/Enzymes, Biomolecules | Polyglutaraldehyde Polymer | U.S. Pat. No. 4,438,239 (Rembaum) U.S. Pat. No. 4,369,226. |
| 10–100 nm | Periodate/Antibody | Dextran | U.S. Pat. No. 5,492,814 (Weissleder) |

The conjugation of annexins to magnetic molecules yields materials that can be used in a variety of fields such as magnetic affinity chromatography, magnetic cell sorting, magnetic immunoassay and as MR imaging contrast agents. The requirements of the particle vary greatly with the intended application. For imaging applications, the magnetic particle must have a series of properties including:

(1) Size and size homogeneity. Magnetic particles are preferably smaller than the size of red blood cells (about 10 microns) to avoid clogging capillary beds. To achieve storage period, which, for practical commercial reasons, is typically longer than 6 months and preferably as long as two years. Instability, evident as the growth in the number of large particles in the preparation, can result in particle induced toxicity, and the abrupt end to the commercial use of the product.

A wide variety of conjugating strategies have been employed to couple proteins to each other and can be adapted to couple Annexins, e.g., Annexin V to magnetic particles, as would be obvious to one skilled in the art. Many of these reagents consist of an N-hydroxysuccinimide ester, which reacts with an amine, and a second moiety that reacts with a sulfhydryl group. A wide selection of bifunctional conjugating reagents, such as SPDP, SMCC, SATA and S1At are available from Piece Chemical Company. Detailed procedures for their use are available from the Piece Chemical web site (see http://www.piercenet.com).

Coupling of Annexin to Optically Active Molecules

Coupling of annexin to optically active molecules may be performed using any of the art known techniques, e.g., those described in U.S. Pat. No. 5,312,922; U.S. Pat. No. 5,928,627; U.S. Pat. No. 6,096,289; Weir, ed., Handbook of Experimental Immunology, Vol. 1, Chapter 28, pp. 28.1–28.21, Oxford, Blackwell Scientific, 1986, the entire contents of each of which are incorporated herein by reference.

Administration of the Annexin Containing Compounds of the Invention

The annexin containing compounds of the present invention may be administered to a subject using standard protocols, such as protocols for the administration of radio-labeled compounds.

The compositions of the invention maybe administered to a subject in an amount effective, at dosages and for periods of time necessary, to achieve the desired result. An effective amount of the compositions of the invention may vary according to factors such as the tumor stage, age, and weight of the subject, and the ability of the composition to elicit a desired response in the subject. An effective amount is also one in which any toxic or detrimental effects (e.g., side effects) of the compositions are outweighed by the therapeutically or diagnostically beneficial effects. The compositions of the invention may be administered at a concentration of 10–1000 $\mu$g protein/kg, 10–900 $\mu$g protein/kg, 10–800 $\mu$g protein/kg, 10–700 $\mu$g protein/kg, 10–600 $\mu$g protein/kg, 10–500 $\mu$g protein/kg, 10–400 $\mu$g protein/kg, 10–300 $\mu$g protein/kg, 10–200 $\mu$g protein/kg, or 10–100 $\mu$g protein/kg.

Annexin V begins to have pharmacological effects (anti-coagulant effects) at doses greater than about 300 $\mu$g/kg. Accordingly, the diagnostic methods of the present invention (which seek to avoid pharmacological effects of the labeled annexin) are preferably practiced at doses lower than 300 $\mu$g/kg, typically less than about 50 $\mu$g/kg. Such tracer doses (e.g., 10 $\mu$g/kg to 50 $\mu$g/kg) have no reported pharmacologic or toxic side effects in animal or human subjects.

The compounds of the invention are typically suspended in a suitable delivery vehicle, such as sterile saline. The vehicle may also contain stabilizing agents, carriers, excipients, stabilizers, emulsifiers, and the like, as is recognized in the art.

The compounds of the invention may be administered to a subject by any suitable route for administration. A preferred method of administration is intravenous (i.v.) injection. It is particularly suitable for imaging of well-vascularized internal organs, such as the heart, liver, spleen, and the like. Methods for i.v. injection of, e.g., radiopharmaceuticals are known. For example, it is recognized that a radiolabeled pharmaceutical is typically administered as a bolus injection using either the Oldendorf/Tourniquet method or the intravenous push method (see, e.g., Mettler and Guierbteau, (1985) *Essentials Of Nuclear Medicine Imaging*, Second Edition, W.B. Saunders Company, Philadelphia, Pa.).

For imaging the brain, the compositions of the invention can be administered intrathecally. Intrathecal administration delivers a compound directly to the sub-arachnoid space containing cerebral spinal fluid (CSF). Delivery to spinal cord regions can also be accomplished by epidural injection to a region of the spinal cord exterior to the arachnoid membrane.

For bronchoscopy applications, the amiexin compounds of the present invention may be administered by inhalation. For example, the annexin compounds may be delivered in the form of an aerosol spray from a pressured container or dispenser which contains a suitable propellant, e.g., a gas such as carbon dioxide, or a nebulizer.

Other modes of administration include intraperitoneal (e.g., for patients on kidney dialysis), and intrapleural administration. For specific applications, the invention contemplates additional modes of delivery, including intramuscular injection, subcutaneous, intralymphatic, insufflation, and oral, intravaginal and/or rectal administration.

Localization of the Annexin Containing Compounds of the Invention

After the compounds of the invention are administered, they are allowed to localize to the target tissue or organ. Localization in this context refers to a condition when either an equilibrium or a pseudo-steady state relationship between bound, "localized", and unbound, "free" compound within a subject has been achieved. The amount of time required for such localization is typically on the order of minutes to tens of minutes and may be estimated by the serum half-life of the compound. The localization time also depends on the accessibility of the target tissue to the compound. This, in turn, depends on the mode of administration, as is recognized in the art.

Imaging is preferably initiated after most of the compound has localized to its target(s). For intravenously administered Tc99m-labeled annexin V, this occurs after several half-lives. A duration of about 10 half-lives (about 30–240 min in the case of annexin/Tc99m conjugates) is considered to be ample time to achieve essentially complete localization. One of skill in the art will appreciate, however, that it may be desirable to perform the imaging at times less than or greater than the ~10 half-life timepoint described above. For example, in imaging cell death due to blood vessel injury, the accessibility of the target tissue is very high, such that a strong signal can be obtained from the target site in only a few minutes, especially if a low dose of labeled annexin is administered gradually to minimize signal from circulating label.

In all of the above cases, a reasonable estimate of the time to achieve localization may be made by one skilled in the art. Furthermore, the state of localization as a function of time may be followed by imaging the gamma ray signal from the labeled annexin according to the methods of the invention.

Applications

Major uses for the annexin containing compounds of the invention include the detection of inappropriate apoptosis in disease states where it should not occur, e.g., immune disorders such as Lupus, transplant rejection, or in cells subject to severe ischemia; and the detection of insufficient apoptosis when it should occur, e.g., tumors or cells infected with a virus.

The annexin containing compounds of the invention may be employed in a variety of clinical settings in which apoptotic and/or necrotic cell death need to be monitored, such as, without limitation, organ and bone marrow transplant rejection or injury, infectious and non-infectious inflammatory diseases, autoimmune disease, cerebral and myocardial infarction and ischemia, cardiomyopathies, atherosclerative disease, neural and neuromuscular degenerative diseases, sickle cell disease, β-thalassemia, cancer therapy, AIDS, myelodysplastic syndromes, and toxin-induced liver disease, and the like. The annexin containing compounds of the invention may also be useful as a clinical research tool to study the normal immune system, embryological development, and immune tolerance and allergy.

The compounds of the invention can be used, for example, to image and quantify apoptotic cell death in normal and malignant tissues undergoing treatment. Monitoring apoptosis with serial imaging studies using these compounds can be used for the rapid testing and development of new drugs and therapies in a variety of diseases. In addition, the methods may be used to monitor the progress of treatment, monitor the progress of disease, or both. Further, they may be used to aid in early detection of certain diseases.

An advantage of the above method is that, by imaging at selected intervals, the method can be used to track changes in the intensity of the emission from the subject over time, reflecting changes in the number of cells undergoing cell death. Such an approach may also be used to track changes in the localization of the compounds of the invention in the subject over time, reflecting changes in the distribution of cells undergoing cell death.

The compositions and methods of the present invention may also be used in the diagnosis and/or treatment of subjects suffering from an eye disease, such as, for example, retinal disease or glaucoma.

The photodynamic therapy (PDT) methods disclosed herein are particularly useful for treating a range of diseases characterized by rapidly growing tissue, including the formation of abnormal blood vessels, such as cancer and age-related macular degeneration (AMD). The type of light source used in PDT varies according to the condition treated. For example, for opthalmology applications, diode laser light may be shone through the slit lamp of a microscope into a subject's eye. For cancer/internal diseases, fiber optics may be used to deliver light to the internal cavities like the lung, the gastro-intestinal tract and esophagus and light-emitting diodes (LED) may be used for skin cancer.

In summary, the compositions and methods of the present invention provide a number of clinical and diagnostic benefits. For example, using the methods of the invention, the response of individual patients to established therapeutic anti-cancer regimens may be efficiently and timely evaluated; the anti-neoplastic activity of new anti-cancer drugs may be evaluated; the optimal dose and dosing schedules for new anti-cancer drugs may be identified; and the optimal dose and dosing schedules for existing anti-cancer drugs and drug combinations may be identified. In addition, using the methods of the invention, cancer patients in clinical trials may be categorized efficiently into responders and non-responders to therapeutic regimens.

The methods of the invention provide, among other things, a non-invasive technique for evaluating the early response of individual patient tumors to chemotherapy. This facilitates the selection of effective treatment by allowing rapid identification of ineffective treatments whose side effects might not be balanced by expected benefits.

The invention is further illustrated by the following examples, which should not be construed as further limiting. The contents of all references, pending patent applications and published patents, cited throughout this application, as well as the Figures are hereby expressly incorporated by reference.

EXAMPLES

Example 1

Attachment of Annexin V to Dextran Coated Magnetic Iron Oxides Through the Use of Periodate Periodate treatment of the dextran coated magnetic particle produces an aldehyde, which forms a Schiff base with the amines of the Annexin V. The complex is stabilized by treatment with sodium borohydride.

A dextran coated superparamagnetic iron oxide nanoparticle was synthesized according to the methods of Molday (1982) *J. Immunol. Methods* 52, 353. Iron oxide (10 mg Fe in about 1 mL of water) and purified Annexin V were dialyzed against sodium acetate (0.01M, pH 6). Annexin V was purified by the method of Wood (1996) *Blood* 88, 1873. The amount of Annexin V can be varied from 1 to about 50 mg, preferably 5–10 mg of protein. At lower amounts the ratio of protein to iron on the resulting magnetic nanoparticle will be lower, but the offered protein will couple more efficiently. At higher amounts of protein, the ratio of protein to iron on the resulting nanoparticle will be higher, but the percent of protein coupled will be lower.

Freshly made sodium periodate (50 mg/mL, 0.2 mL) was added to the iron oxide. The mixture was then incubated for 30 minutes at room temperature in the dark, and dialyzed against 0.15 M NaGI. The oxidized magnetic iron oxide was then mixed with the Annexin V and the pH adjusted by the addition of 100 μl of 0.2 M sodium bicarbonate, pH 9.5. The mixture was incubated for 3 hours with stirring. Freshly made sodium cyanoborohydride was then added (25 mg/mL, 0.2 mL) and the mixture was incubated for 6 hours at room temperature. The Annexin V-magnetic nanoparticle can be separated from the unreacted Annexin by a variety sized based separation methods. These include gel filtration, ultra-filtration or magnetic separation.

Example 2

Attachment of Annexin V with a Sulfhydryl Group to Amino CLIO

The amino-CLIO nanoparticle was made as described in Josephson (1999) *Bioconjug. Chem.* 10, 186. Annexin V with a sulfhydryl group added through mutagenesis (Tait (2000) *Bioconjug Chem* 11, 918) was employed. To 1.2 mL of amino-CLIO in (30 mg Fe) was added 1.2 mL of 0.1 M phosphate buffer, pH 7.4, and 2 mL of N-succinimidyl 3-(2-pyridyldithio)propionate (SPDP, 25 mM) (Molecular Bio-sciences, Boulder, Colo.) in DMSO. The mixture was allowed to stand for 60 minutes at room temperature. Low molecular impurities were removed by PD-10 columns (Sigma Chemical, St- Louis, Mo.) equilibrated with 0.01 M Tris and 0.02 M citrate, pH 7.4 buffer.

Between 2 and 50 mg of Annexin V was subsequently added to 10 mg Fe of the SPDP activated nanoparticle at room temperature arid the mixture was allowed to stand overnight. The Annexin V-magnetic nanoparticle can be separated from the unreacted annexin by a variety sized based separation methods.

Example 3

Reaction of Annexin V to Add a Sulfhydryl Group, Followed by Reaction with Amino CLIO A sulfhydryl group was added to the annexin (obtained as in Example 1) by use of the reagent SATA following the manufacturers instructions, Pierce Chemical Company. Amino-CLIO was reacted with SPDP as in Example 2 and then reacted with the SATA reacted annexin.

Example 4

Attachment of Annexin V to a BSA Coated Magnetic Particle

BSA coated magnetic particles were made as described in U.S. Pat. No. 4,795,698. Some of the amine groups of the BSA coating of the magnetic particle are converted to sulfydryl groups by use of the reagent SPDP (see Example 2). SPDP or SATA can then be used to add one or more sulfydryl groups on Annexin V. After treatment of the Annexin V with DTT, to expose a sulfhydryl group, the protein is reacted with the magnetic particle.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A composition comprising an annexin or a fragment thereof coupled to an optically active molecule, wherein said optically active molecule is selected from the group consisting of PHOTOFRIN®, Lutrin, ANTRIN®, FOSCAN®, aminolevulinic acid, aluminum (III) phthalocyanine tetrasulfonate, Hypericin, verteporfin, and methylene blue dye.

2. The composition of claim 1, wherein the optically active molecule is aminolevulinic acid.

3. The composition of claim 1, wherein the optically active molecule is PHOTOFRIN®.

4. The composition of claim 1, wherein the optically active molecule is Lutrin.

5. The composition of claim 1, wherein the optically active molecule is ANTRIN®.

6. The composition of claim 1, wherein the optically active molecule is FOSCAN®.

7. The composition of claim 1, wherein the annexin is annexin V.

8. A method of tumor photodynamic therapy, comprising administering to a subject bearing a tumor a composition comprising annexin or a fragment thereof coupled to an optically active molecule; and illuminating the subject with a light source in the presence of oxygen, thereby creating a toxic form of oxygen that destroys the tumor.

9. The method of claim 8, wherein the composition is administered at a concentration of 1–500 µg protein/kg.

10. The method of claim 8, wherein the composition is administered at a concentration of 1–400 µg protein/kg.

11. The method of claim 8, wherein the composition is administered at a concentration of 1–200 µg protein/kg.

12. The method of claim 8, wherein the composition is administered via a method selected from the group consisting of intraperitoneally, intrathecally, intrapleurally, intralymphatically and intramuscularly.

13. The method of claim 8, wherein the tumor is present in an organ of a subject or a portion thereof.

14. The method of claim 8, wherein the tumor is present in the head of a subject or a portion thereof.

15. The method of claim 8, wherein the tumor is present in the heart of a subject or a portion thereof.

16. The method of claim 8, wherein the tumor is present in the liver of a subject or a portion thereof.

17. The method of claim 8, wherein the tumor is present in the eye of a subject or a portion thereof.

18. The method of claim 8, wherein the optically active molecule is selected from the group consisting of PHOTOFRIN®, Lutrin, ANTRIN®, FOSCAN®, aminolevulinic acid, aluminum (III) phthalocyanine tetrasulfonate, Hypericin, verteporfin, and methylene blue dye.

19. The method of claim 8, wherein the toxic form of oxygen is singlet oxygen.

20. The method of claim 8, wherein the tumor is selected from the group consisting of a brain tumor, a head tumor, a neck tumor, a breast tumor, an esophagus tumor, a lung tumor, a pleural cavity tumor, an ovary tumor, an abdominal cavity tumor, a bladder tumor, a prostate tumor, a cervix tumor, and a skin tumor.

* * * * *